United States Patent [19]

Martin et al.

[11] 4,435,268

[45] Mar. 6, 1984

[54] OXYGEN SENSING CELL

[75] Inventors: Gordon W. Martin, Ronceverte; John Strohl, Morgantown, both of W. Va.

[73] Assignee: The Bendix Corporation, Southfield, Mich.

[21] Appl. No.: 411,765

[22] Filed: Aug. 26, 1982

[51] Int. Cl.³ ............................................ G01N 27/50
[52] U.S. Cl. .................................... 204/408; 204/412; 204/415
[58] Field of Search ............... 204/408, 411, 412, 415, 204/1 P; 128/635

[56] References Cited

U.S. PATENT DOCUMENTS

| | | | |
|---|---|---|---|
| 3,239,444 | 3/1966 | Heldenbrand | 204/415 |
| 3,246,235 | 4/1966 | Allsopp | 324/195 |
| 3,328,277 | 6/1967 | Solomons et al. | 204/412 |
| 3,334,039 | 8/1967 | Vlasak | 204/195 |
| 3,429,796 | 2/1969 | Lauer | 204/195 |
| 3,454,485 | 7/1969 | Hauk et al. | 204/415 X |
| 3,510,420 | 5/1970 | Mills | 204/195 |
| 3,518,179 | 6/1970 | Bleak et al. | 204/195 |
| 3,526,577 | 9/1970 | Molloy | 204/415 X |
| 3,575,836 | 4/1971 | Sternberg | 204/195 |
| 3,668,101 | 6/1972 | Bergman | 204/195 |
| 3,689,394 | 9/1972 | Davies et al. | 204/195 P |
| 3,755,125 | 8/1973 | Shaw et al. | 204/195 P |
| 3,767,552 | 10/1973 | Lauer | 204/408 |
| 3,847,777 | 11/1974 | Haddad et al. | 204/195 P |
| 4,057,478 | 11/1977 | Bruckenstein et al. | 204/195 P |
| 4,078,981 | 3/1978 | Neti et al. | 204/195 P |
| 4,126,531 | 11/1978 | Porter et al. | 204/408 |
| 4,166,775 | 9/1979 | Bruckenstein et al. | 204/1 T |
| 4,259,165 | 3/1981 | Meyake | 204/195 P |
| 4,268,370 | 5/1981 | Neti . | |
| 4,324,257 | 4/1982 | Albarda et al. | 204/412 X |

Primary Examiner—G. L. Kaplan
Attorney, Agent, or Firm—Bruce L. Lamb; W. G. Christoforo

[57] ABSTRACT

An improved oxygen sensing cell, especially of the polarographic type, is intended for use primarily in a gaseous environment. The cell has a cathode located at the bottom of the cell body. The cathode comprises a gold mesh electrode laminated to a thin-film sense membrane. The electrode is thus made immobile relative to the membrane, thereby improving the response time and providing for long-term sensor stability. The cell further has a guard electrode for the cathode. The guard electrode operates continuously and scavenges any oxygen molecules which are dissolved in the electrolyte and diffused towards the cathode. As a result, the dynamic range of the cell is substantially increased. The anode comprises a silver wire wound about a spool retained within the main cavity in the cell body. A p.c. board, as well as a compensation membrane, are resiliently retained at the top of the cell body. The body carries conductors for electrically connecting the p.c. board with the anode, cathode, and guard electrode, respectively.

6 Claims, 11 Drawing Figures

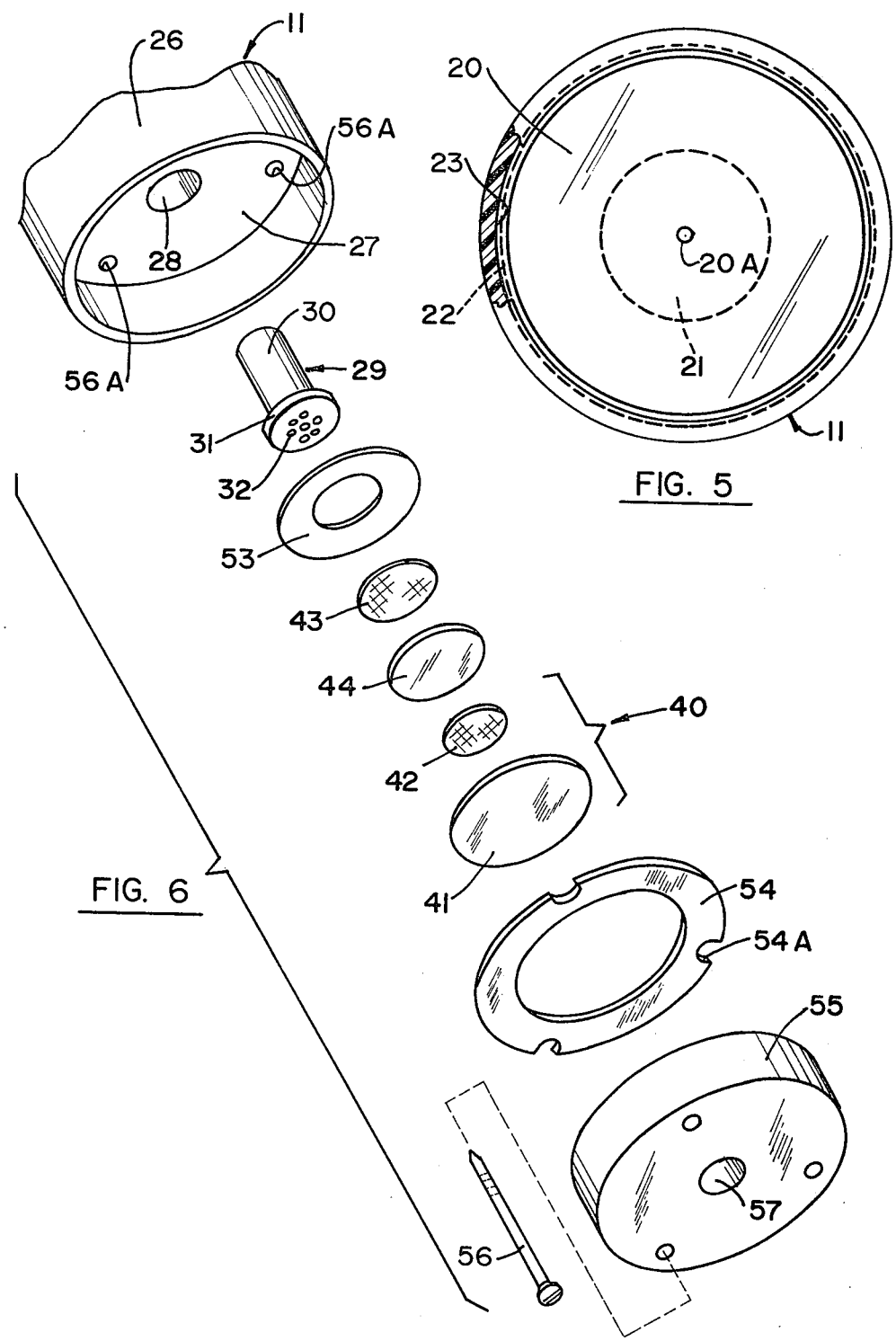

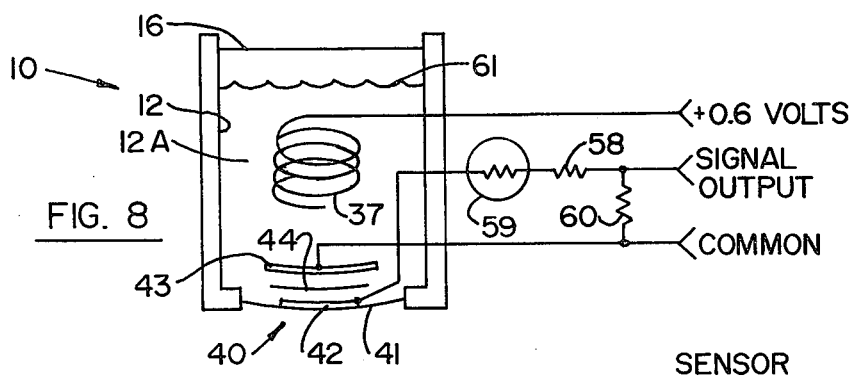
FIG. 8
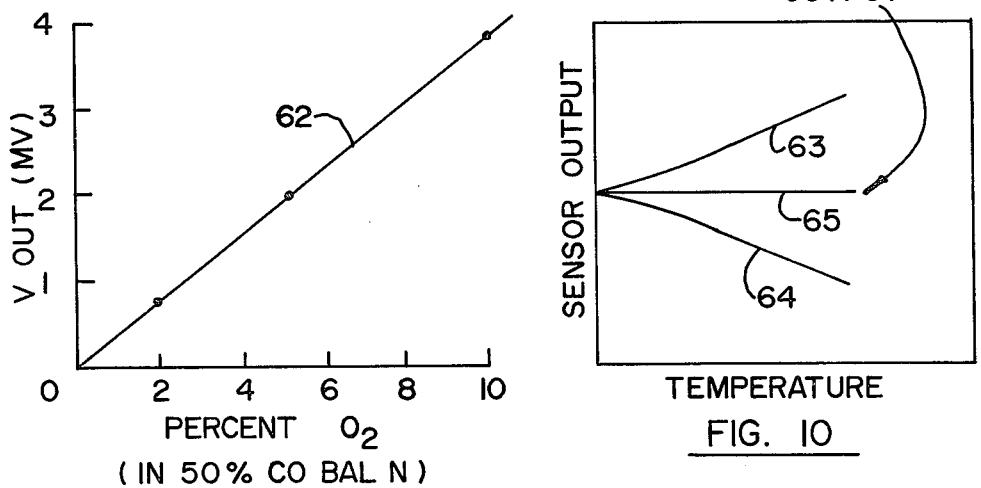
FIG. 9
FIG. 10
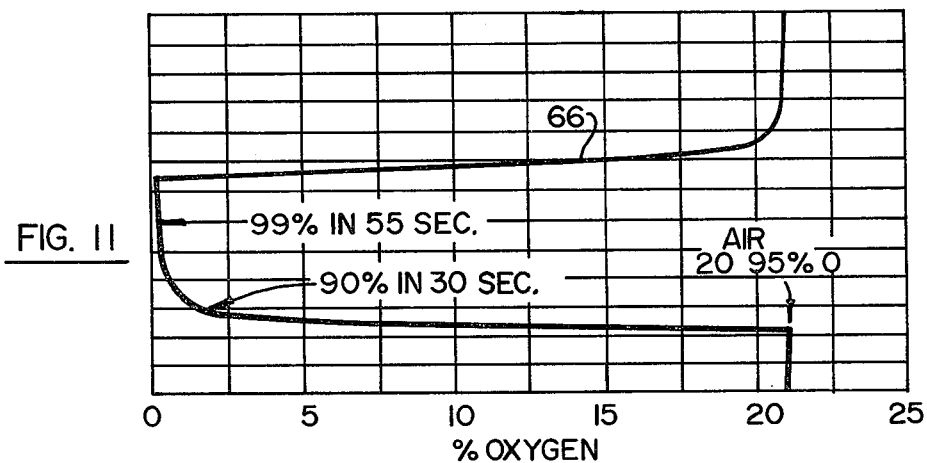
FIG. 11

OXYGEN SENSING CELL

FIELD OF THE INVENTION

The present invention relates to an oxygen sensing cell especially adapted for use in a gaseous environment, and more particularly, to an improved polarographic oxygen sensing cell which has an improved long-term stability, an increased dynamic range, a longer shelf life as well as a longer operational life, yet is compact, reliable, easily replaceable, and relatively inexpensive to manufacture.

BACKGROUND OF THE INVENTION

Oxygen sensing cells are well known in the prior art. Their purpose is to monitor the oxygen level in a gas or liquid. These cells are electrochemical in their operation and are arranged to generate an output signal whenever the oxygen level in the sample being monitored reaches a predetermined threshold value. The output signal triggers an electronic circuit for activating an alarm or adjusting a process. For example, the cells may be used for detecting potentially dangerous levels of oxygen in a combustible gas, or for on-line monitoring of oxygen in a chemical or petrochemical plant process stream.

In general, there are two types of oxygen sensing cells using electrochemical techniques. One is the galvanometric cell which generates its own signal current whenever oxygen molecules pass through its membrane. These cells are similar to miniature fuel cells. The other type of sensing cell is polarographic, that is, it is polarized by an external voltage source.

Construction wise, these polarographic oxygen sensing cells generally consist of a body having a main cavity containing a suitable electrolyte. The body may be closed at one end and covered at the other end by a stretched membrane. This membrane, which may be made of polyethylene or other suitable material, is liquid-impermeable but gas-permeable. It thus seals the liquid electrolyte within the cell, but permits the gas being sampled to pass into the cell. An anode is mounted within the cavity and cooperates with a cathode mounted on the cell body internally of the membrane. By way of example, the anode may be made of silver, the cathode of gold, and the electrolyte may consist of a potassium chloride solution. Suitable respective conductors are carried by the body for connecting the anode and cathode to external circuitry. A positive bias is placed on the anode, thereby polarizing the cell, and the output signal is developed between the cathode and ground to obtain the desired measurement.

While generally satisfactory for the purposes intended, these prior art designs and constructions have certain inherent disadvantages or deficiencies; and thus the need has continued to exist for an improved oxygen sensing cell, one which has a substantially improved long-term stability, dynamic range and life, as well as other desirable characteristics.

SUMMARY OF THE INVENTION

Accordingly, it is an object of the present invention to provide an improved oxygen sensing cell, and especially an improved polarographic oxygen sensing cell, one that alleviates the disadvantages and deficiencies of the prior art and fulfills the existing need for improved stability, life, performance and reliability.

It is another object of the present invention to provide an improved polarographic oxygen sensing cell for use in a gaseous environment, including a guard electrode for the cathode, thereby increasing the dynamic range of the cell by an order of magnitude.

It is yet another object of the present invention to provide an improved cell having a cathode comprising a sense membrane laminated to a mesh electrode, thereby substantially improving the long-term stability of the cell and providing for a consistently fast response.

It is a further object of the present invention to provide an improved cell which is relatively insensitive to, hence not affected by, the presence of carbon dioxide in the gas being sampled.

It is a still further object of the present invention to provide, in a polarographic oxygen sensing cell of the character described, a temperature compensating means for rendering the sensor output relatively constant over the range of ambient temperatures encountered during operation of the cell.

It is, again, another object of the present invention to provide an oxygen sensing cell having a longer shelf life as well as improved operational life.

It is again a further object of the present invention to provide an improved oxygen sensing cell which is relatively compact, easily replaceable, reliable, and relatively inexpensive to manufacture.

In accordance with the broad teachings of the present invention, the sense membrane is made immovable in relation to the cathode. In the preferred embodiment, this is achieved by directly laminating a porous gold or gold-plated cathode to the thin-film membrane. The lamination process is preferably conducted under heat and pressure. As a result, sensor stability and response time are considerably improved. In addition, a guard electrode is preferably mounted between the cathode and the opening in the cell body. This guard electrode operates continuously and scavenges any oxygen molecules which are dissolved in the electrolyte and are diffused towards the cathode. As a result, the dynamic range of the cell is substantially increased.

In accordance with the still further teachings of the present invention, the improved sensing cell has a superior overall construction. This construction includes a button having a hollow sleeve portion mounted within the opening leading into the cavity in the generally cylindrical cell body. A spool has an axial opening press-fitted over the sleeve portion of the button, coaxially thereof, thereby retaining the spool in the cavity. The anode preferably comprises a silver wire wound about the spool. A compensation membrane is mounted on an annular ledge formed in the other end of the body, and an O-ring is placed on top of the membrane. A printed circuit ("p.c.") board is placed on top of the O-ring. A top disc is mounted on the body for sealing the electrolyte therein. This top disc has a portion engaging the p.c. board, thereby resiliently retaining the p.c. board and the compensation membrane The cell body carries conductors for electrically connecting the p.c. board with the anode, cathode, and guard electrode, respectively.

These and other objects of the present invention will become apparent from a reading of the following specification, taken in conjunction with the enclosed drawings.

BRIEF DESCRIPTION OF THE DRAWINGS

FIG. 5 is a section view, taken along the lines 5—5 of FIG. 1, showing the manner in which the top disc is snapped into the opening in the body;

FIG. 6 is an exploded perspective, showing the cathode, guard electrode, and the other components positioned at the bottom of the body;

FIG. 8 is a schematic diagram of the sensing cell, showing part of the electrical circuitry associated therewith;

FIG. 9 is a graph showing the substantially linear output of (a preferred embodiment of) the sensing cell in the presence of carbon dioxide;

FIG. 10 is a graph showing the effects of a temperature-compensating thermistor in the associated circuitry; and FIG. 11 is a graph showing the relatively-fast sensor response time.

DESCRIPTION OF THE PREFERRED EMBODIMENT

Figure 1:
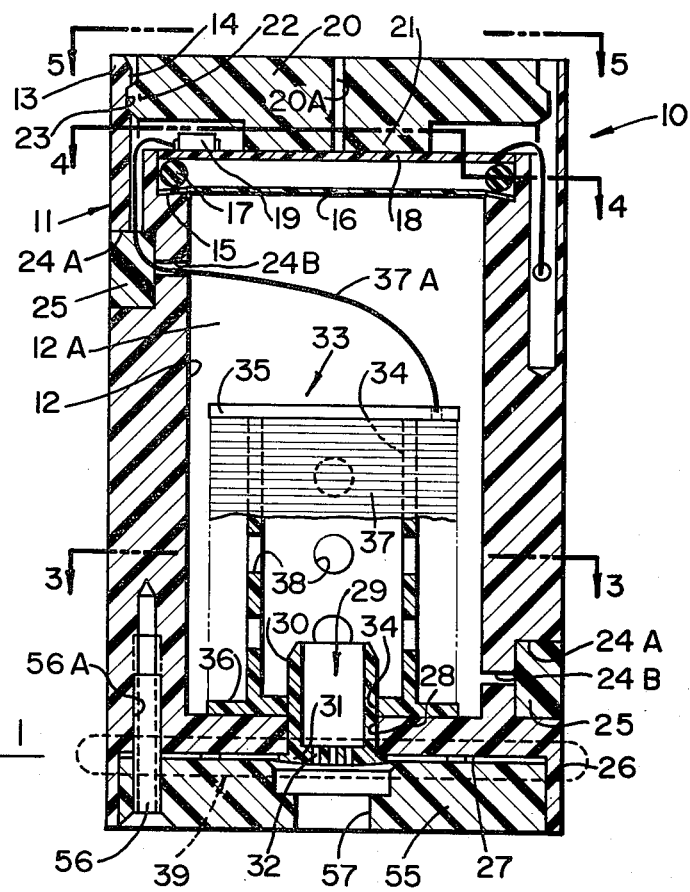
FIG. 1 is a longitudinal section of the improved oxygen sensing cell of the present invention, the assembly of the cathode, guard electrode and associated parts being illustrated schematically by the broken lines.

With respect to FIGS. 1-7, there is illustrated a preferred embodiment of the improved polarographic oxygen sensing cell 10 of the present invention, one intended primarily for use in a gaseous environment. It will be appreciated by those skilled in the art, however, that the teachings of the present invention are equally applicable to galvanometric cells as well as oxygen sensing cells for use in a liquid environment. With this in mind, the cell 10 has a body 11, preferably cylindrical, having a height of 2.5 inches and a diameter of 1.5 inches in the preferred embodiment. The cylindrical body is fabricated from a suitable plastic material. The plastic material should provide machinability and toughness for ease of manufacturing and assembly, have good impact strength, and yet be resistant to chemical attack or adverse reactions. One such material meeting these criteria is "DELRIN" manufactured and sold by Dupont. The cell body 11 has an axial bore 12 forming a main cavity 12A for the cell. This main cavity 12A is filled with a suitable electrolyte, such as potassium chloride (KCl). The body further has a top portion 13 with a counterbore 14 formed therein connecting with the bore. An internal annular ledge 15 is formed between the bore and counterbore (and is preferably inclined as shown in FIG. 1). A compensation membrane 16 is seated on the annular ledge. This compensation membrane preferably comprises a polytetrafluoroethylene ("PTFE") film having a thickness of approximately 2.0 mils. A suitable film is sold by Dupont under the trademark "TEFLON". An O-ring 17 is seated on top of the compensation membrane. A printed circuit ("p.c.") board 18 is seated on top of the O-ring. The p.c. board 18 has the desired electrical components, designated generally at 19. A top disc 20 is secured within the top portion of the cell and is provided with a vent hole 20A. The top disc 20 has a central portion 21 which bears against the top of the p.c. board, and through the p.c. board, applies a force against the O-ring. With this arrangement, the compensation membrane is maintained in a stretched position over the main cavity, and the p.c. board is resiliently retained in the body. Preferably, the top disc has an external annular bead 22 adapted to be received within an internal annular groove 23 formed in the counterbore of the body, whereby the top disc may be snapped into the body and retained therein. The top disc is formed from a suitable plastic material (which may also be "DELRIN") and forms a top seal for the electrolyte in the cell. Two pairs of communicating access openings 24A and 24B are formed at the top and bottom, respectively, in the cylindrical wall of the cell body. After the cell has been assembled (as hereinafter described) the cell may be inverted and the electrolyte may be poured into the cavity through the bottom openings. Opening 24A at the top is previously sealed by plug 25. When the cavity is filled with the electrolyte, the opening 24A at the bottom is also sealed by a respective plug 25. These plugs 25 may be formed from a suitable compound, such as a room-temperature vulcanizable elastomeric material (known as "RTV").

Figure 2:
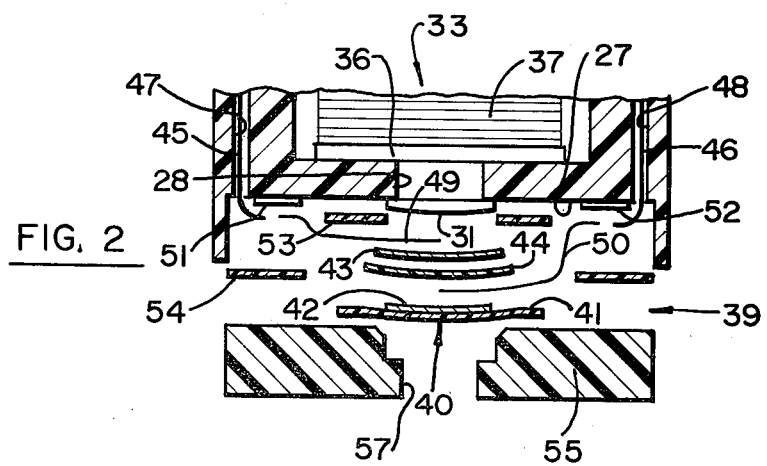
FIG. 2 corresponds substantially to the bottom portion of FIG. 1, but is displaced therefrom circumferentially by ninety degrees about the axis of the cylindrical cell body, and (in partial schematic form) shows the cathode and guard electrode, the respective conductors thereto, and the associated parts in exploded relationship to one another and to the cell body.
Figure 3:
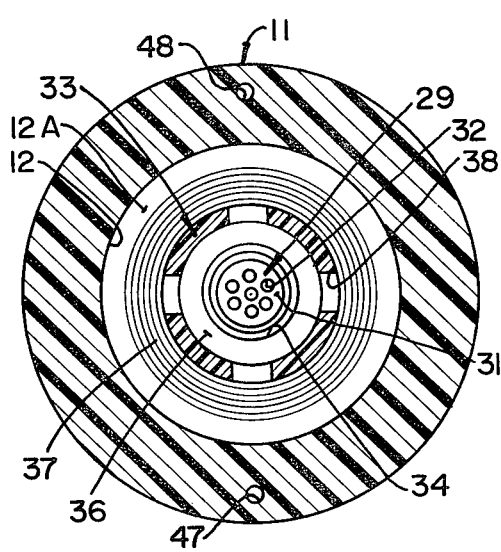
FIG. 3 is a detail section view, taken along the lines 3—3 of FIG. 1, showing the hollow spool for the coiled wire anode, the spool being press-fitted coaxially on the sleeve portion of the button.
Figure 4:
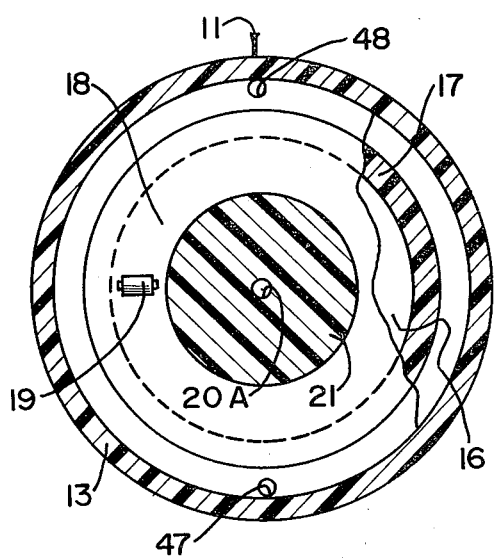
FIG. 4 is a stepped section view, taken along the lines 4—4 of FIG. 1, showing the means for resiliently retaining the printed circuit board in the cell body.
Figure 7:
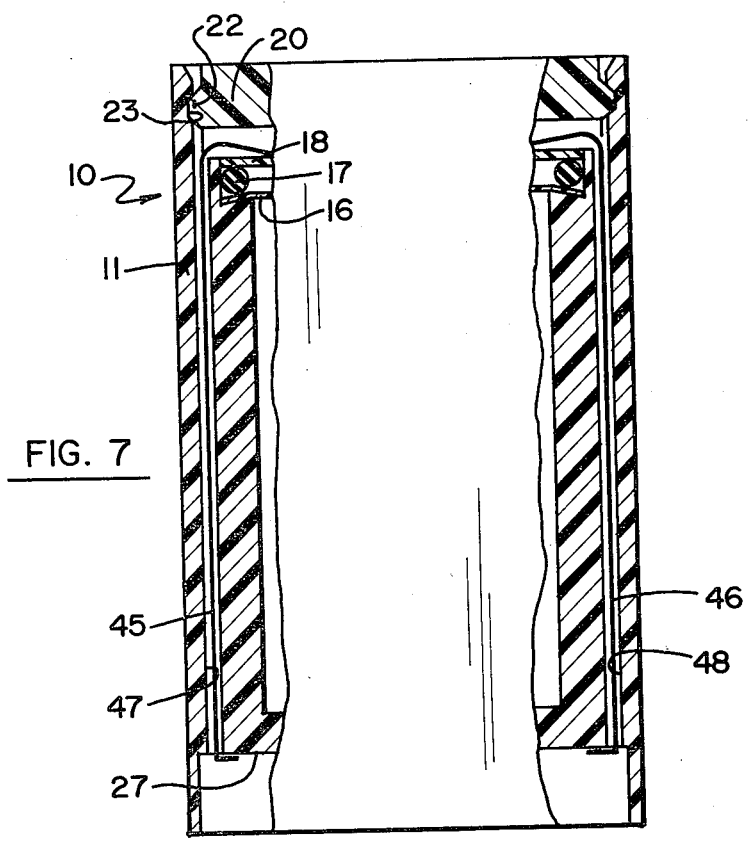
FIG. 7 is a further longitudinal section of the cell, corresponding substantially to FIG. 1, but taken in a plane displaced by ninety (90) degrees therefrom, and showing the conductors carried by the cell body.

With further reference to FIGS. 1-7, the cell body has a bottom portion 26 axially spaced from the top portion and provided with an end face 27. The end face has a central opening 28 leading into the main cavity in the cell body. A push-in button 29 has a sleeve portion 30 press-fitted within the opening and extending into the main cavity of the body. The button is further provided with a head 31 having a plurality of apertures 32. A hollow spool 33 is nested coaxially on the sleeve portion of the button. Preferably, the spool has an opening 34 press-fitted over the sleeve, thereby frictionally retaining the spool in the cavity. The spool has top and bottom flanges 35 and 36, respectively. An anode 37 is mounted on the spool. Preferably, the anode 37 comprises a wire 37A formed from a suitable silver compound. The wire 37A passes through access openings 24A, 24B at the top of the cell body; and the wire is wound helically around the spool, between the flanges thereof, and includes several layers as shown in FIG. 3. The spool has a series of apertures 38 for assuring the proper contact between the anode and the liquid electrolyte. Preferably, the button and spool are also formed from "DELRIN", although other materials are feasible.

The overall cathode and guard electrode structure is located at the bottom portion of the cell body, as shown schematically by the broken lines 39 in FIG. 1. This overall structure 39, as shown in FIG. 2, includes a cathode 40 across the central opening 28. This cathode 40 constitutes a sensing means for the cell and comprises an outer permeation sense membrane 41 secured to an inner mesh electrode 42. Preferably, the membrane and electrode are laminated together under the application of heat and pressure. In the preferred embodiment, the sense membrane comprises a one (1) mil polytetrafluoroethylene film (sold by Dupont under the trademark "TEFLON") and the mesh electrode 42 is a fine mesh gold screen. This gold mesh electrode 42 is approximately 0.25 inches in diameter and is laminated to the central portion of the sense membrane.

Thus, the sense membrane 41 is made immobile with respect to the cathode (electrode 42) for improved long-term stability (without requiring continuous recalibration) as well as faster response time (as hereinafter illustrated). The surface of the electrode 42 is sufficiently porous so that an interface of membrane wall, gold cathode, and aqueous electrolyte exists. This stable "triple" interface at the surface of the sense membrane maximizes the sensor response time and sensitivity, since the oxygen molecule reduction reaction does not occur until it has diffused through the membrane and electrolyte solution to reach the cathode. As a result, the problem (in the prior art) of stretching a sense membrane over a separate gold cathode—to achieve an intimate membrane-cathode-electrolyte contact—is eliminated. This is another important advantage of the present invention over the prior art.

In the preferred embodiment, a guard electrode 43 is mounted between the central opening 28 and the cathode 40. Preferably, the guard electrode 43 comprises a gold mesh disc which is approximately 9/16" in diameter and has approximately 500 lines per inch. The guard electrode 43 is electrically insulated from the cathode by means of a nylon screen 44 which also serves as a filter. The guard electrode 43 operates continuously to scavenge any oxygen molecules which may be dissolved in the electrolyte and which are diffused towards the cathode, thereby substantially increasing the dynamic range of the cell.

With reference again to FIGS. 2, 6 and 7, the cell body 11 carries a pair of conductors 45, 46 located in respective passageways 47, 48 formed in the body. In the preferred embodiment, the conductors are 32-gauge tinned copper wires. One end of each respective conductor is connected to the p.c. board at the top of the cell. The other ends of the conductors extend slightly beyond the end face of the bottom portion of the cell body, and are connected to respective connecting wires 49, 50 by means of respective conductive tape pads 51, 52. These conductive tape pads 51, 52 have an adhesive backing, thereby retaining the pads to the cell body, and the wires are in turn soldered to the pads. In the preferred embodiment, the wires 49, 50 are fine gold wires having a diameter of 0.003 inches. Wire 49 connects conductor 45 to the guard electrode 43, while wire 50 connects conductor 46 to the gold mesh electrode 42 (of the cathode 40). A first compression ring 53, preferably comprising a small flat fluorocarbon washer, is located concentrically about the guard electrode 43 and holds wire 49 against the bottom face 27 of the cell body. A second compression ring 54, preferably comprising a large flat fluorocarbon washer, is located concentrically of the first ring 53 and radially thereof. This second ring 54 holds a portion of wire 50 against the bottom face of the cell body. As shown more clearly in FIG. 2, the remaining portion of wire 50 runs (radially) between the first and second compression rings and substantially along the outer face of the first compression ring 53. A bottom disc 55 is secured to the cell body by a plurality of screws 56 (preferably three) as shown more clearly in FIG. 6. The screws pass through openings 54A in compression ring 54 and are received in tapped openings 56A in the cell body, thereby retaining the cathode 40, guard electrode 43, insulating filter screen 44 and compression rings 53, 54 against the bottom face 27 of the cell body 11. This bottom disc 55 has a central opening 57 formed therein, through which the cathode is accessible externally of the cell body for sensing the presence of oxygen in gas samples or in ambient air.

With reference to the schematic electrical diagram of FIG. 8, a positive polarizing voltage (of preferably 0.6 volts) is applied to the silver anode. This voltage is selected to be above the potential necessary for oxygen reduction at the cathode, but below that for the electrolysis of water. The electrolyte system (comprising a neutral KCl solution 61 with the silver anode 37) is chosen so as not to react with carbon dioxide ($CO_2$) in the gas being sampled or monitored. In the preferred embodiment, the thickness of the cathode is such, that with a "TEFLON" sense membrane, the output current for air is about fifteen (15) microamps. This output current is fed through the internal resistor 58 and thermistor 59. The resultant voltage, developed across the resistor 60, constitutes the signal output of the cell. This signal output is transmitted to an input amplifier and other electronic circuitry, which (being conventional) have been omitted for ease of illustration. The function of the thermistor is to compensate for the temperature coefficient of the membrane diffiusion rate of the cathode (as hereinafter illustrated).

With reference to FIG. 9, there is illustrated the response of the preferred embodiment of the present invention, that is, the improved polarographic sensing cell 10 at various oxygen concentrations in samples containing fifty percent (50%) of carbon dioxide ($CO_2$). By operating at a properly selected polarizing voltage, the sensing cell is made insensitive to $CO_2$ in the sample. The sensor polarizing voltage is maintained, and there is no need for a special sensing cell for measurement in streams containing $CO_2$. As indicated by the line 62 in FIG. 9, cell response is substantially linear, that is, the voltage level of the output signal is directly proportional to the oxygen concentration in the gas being sampled, regardless of the presence of a substantial concentration of $CO_2$ in the gas. This is still another important advantage of the present invention.

With reference to FIG. 10, oxygen diffusion through the sense membrane 41 is temperature dependent by about plus two-and-a-half percent per degree centigrade (+2.5%/°C.). This is illustrated by the curve 63, which is the uncompensated sensor output. Accordingly, it is possible to adjust the resistor-thermistor network 58, 59 so as to have a generally equivalent, but negative, temperature coefficient (as shown by the curve 64) so as to compensate for this effect. As a result, the sensor output is properly compensated for and is substantially "flat", that is, temperature insensitive over its operating range (as illustrated by the straight line 65 in FIG. 10).

With reference to FIG. 11, the response time of the improved sensing cell is illustrated by the line 66. The speed of the response to a step change in oxygen flowing past the sense membrane 41 is primarily dependent on two factors: first, the thickness of the membrane; and second, how closely the cathode mesh electrode (being wetted by the liquid electrolyte) contacts the inside surface of the membrane. By providing a "composite" cathode subassembly, comprising a gold mesh electrode 42 suitably laminated to the sense membrane 41, the problem of proper contact between the electrode and the membrane has been obviated. As a result, the sensing cell of the present invention exhibits a consistently fast response for a given membrane thickness.

Thus, it will be appreciated by those skilled in the art that the improved polarographic sensing cell of the present invention has a number of significant advantages and features (heretofore not available in the prior art). These advantages and features may be enumerated as follows: (1) the sense membrane is made immovable in relation to the cathode, thereby improving sensor stability and obviating the problem of stretching a membrane over a separate cathode; (2) the guard electrode assures higher accuracy and lower standing current; (3) the sensor has a relatively long operational life plus improved reliability; (4) there is no $CO_2$ interference and hence no buffers are required; (5) only one sensing cell is required, regardless of background; (6) the sensor does not operate unless the voltage is applied, thereby assuring a relatively long shelf life; (7) the sensing cell is easily replaced in the overall monitoring apparatus; (8) the cell exhibits long operational life due to low rate of $H_2O$ evaporation loss through the sense membrane, an advantage gained from its small surface area compared to prior art; and (9) the sensing cell is relatively compact, lightweight, and inexpensive to manufacture.

With reference again to the schematic drawing of FIG. 8, the sensor electrochemistry (of the improved cell of the present invention) may be more readily understood. The polarographic technique of measuring oxygen is obtained by the use of a driving potential sufficient to cause an apparent current flow through an electrolyte in the presence of dissolved oxygen. Two electrodes are immersed in the electrolyte and the interconnecting circuit serves as the source of the driving potential and as a means of measuring the current flow as the result of oxygen becoming present. In the preferred embodiment, and as previously described, silver is used as the anode (+) and gold as the cathode (−). The electrolyte furnishes the available ions to allow current to flow from the silver anode to the gold cathode.

When oxygen is added to the electrolyte, the following reaction occurs at the silver anode. The driving potential furnishes four silver ions to react with four chloride ions available in the potassium chloride (KCl) electrolyte. This reaction forms four silver chloride molecules and releases four electrons according to the following equation:

$$4Ag^+ + 4Cl^- = 4AgCl + 4e^-$$

The four electrons flow through the power supply to the gold cathode to allow the reduction of the oxygen to take place, as follows:

$$O_2 + 2H_2O + 4e^- = 4OH^-$$

The produced hydroxyl ions act as substitutes for the chloride ions consumed at the anode. The resultant current flow is proportional to amount of oxygen molecules that reach the cathode.

The signal current from the cathode passes through resistors mounted inside the cell body, providing a signal voltage of about 12 millivolts when measuring air. Sensor sensitivity is determined as follows:

$$\frac{12 \text{ mv}}{20.95\% \text{ } O_2} = \frac{12 \text{ mv}}{209500 \text{ ppm } O_2} = .05 \frac{\mu v}{\text{ppm } O_2}$$

In the preferred embodiment, the input amplifier guarantees an input offset voltage drift of less than 0.05 $\mu v/°C$. This results in amplifier temperature errors equivalent to less than 1 ppm $O_2/°C$. For an oxygen analyzer having a full scale range of 1%, this represents an electronic error of only 0.01% of full scale per °C.

The ability of the oxygen to diffuse through the sense membrane 41 is dependent upon the partial pressure of oxygen in the sample and the temperature of the membrane itself. Since the oxygen on the electrolyte side of the membrane is consumed on the gold mesh electrode 42, there will exist a maximum differential pressure (at atmospheric sample pressure) of approximately 160 mm Hg at 21% oxygen. This differential pressure is proportional to the partial pressure of oxygen in the sample.

The electrochemical oxygen sensors (of the prior art) have the undesirable characteristic of continuing to consume themselves, even when not in use. A sealed bag will retard, but not stop this phenomenon. This is a limiting factor on shelf life. The sensing cell of the present invention does not substantially deplete itself until it is actually installed. When sealed in a low-moisture permeation bag, it will have a relatively long shelf life. This long shelf life is an important consideration for spare parts utilization and maintenance purposes.

With respect to electrolyte evaporation, a thin sense membrane is desirable from a response speed and sensitivity standpoint, since both these functions are inversely proportional to membrane thickness. Evaporation loss is greater with a thin membrane, so the membrane thickness must be balanced between these extremes. It is also true that the membrane and cathode surface areas should be small to further reduce the evaporation loss. The worst case for electrolyte evaporation is encountered when making oxygen measurements in a low dew point sample stream. In the preferred embodiment, weight loss tests conducted by operating oxygen sensors in a dry sample stream indicate tnat evaporation will not affect sensor operation for at least 24 months of service.

With respect to sacrificial electrode depletion, oxidation depletes the silver at a rate proportional to the oxygen being measured. Each silver atom provides one electron when oxidized to silver chloride. Knowing the signal current flow, determined by cathode area, produced by 100% $O_2$ and assuming one year life, it is possible to calculate the amount of silver required in the anode wire.

Obviously, many modifications may be made without departing from the basic spirit of the present invention. Accordingly, it will be appreciated by those skilled in the art that within the scope of the appended claims, the invention may be practiced other than has been specifically described herein.

We claim:

1. An oxygen sensing cell, comprising a body having a pair of end portions provided with respective first and second openings therein, the body further having a central bore forming a main cavity communicating with the openings, an electrolyte within the cavity, a compensation membrane mounted over the first opening in the body, an anode within the cavity in the body, a cathode across the second opening in the body and including an outer permeation sense membrane and an inner porous electrode bonded to the inner surface of said sense membrane, a guard electrode between the second opening and the cathode, said guard electrode being substantially coextensive with and overlying said inner porous electrode, a thin layer of insulating material which is pervious to said electrolyte interposed between said guard electrode and said porous electrode, the opposite sides of said insulating layer being in intimate contact with the adjacent surfaces of said guard electrode and said porous electrode so that said guard electrode is spaced from said porous electrode only by said insulating layer, the guard electrode operating continuously, whereby oxygen molecules dissolved in the electrolyte and diffusing towards the cathode will be scavenged by the guard electrode, thereby substantially increasing the dynamic range of the sensing cell, and means within the body for respectively establishing electrical connections to the anode, cathode and guard electrode.

2. An oxygen sensing cell, comprising a body having a central cavity with at least one opening communicating therewith, an electrolyte within the cavity, a spool concentrically mounted within the cavity and having an opening communicating with the opening in the body, a button having a sleeve portion mounted within the body opening and coaxially aligned with the spool opening, the button further having a head portion provided with at least one aperture communicating with the bore in the spool, an anode including a helical wire wound about the spool, a cathode outwardly of the head portion of the button and including an outer permeation sense membrane and an inner mesh electrode, and a guard electrode between the head of the button sleeve and the cathode and insulated therefrom.

3. In an oxygen sensing cell, the combination of a body having a bore and a connecting counterbore, an electrolyte within the bore, an annular ledge between the bore and counterbore, a compensation membrane mounted on the ledge, an O-ring on top of the membrane, a p.c. board on top of the O-ring, and a top disc secured within the counterbore of the body and having a portion bearing against the p.c. board, thereby resiliently retaining the p.c. board and the membrane in the body, and thereby forming a top seal for the electrolyte in the cell cavity.

4. In an oxygen sensing cell, the combination of a body having a bottom face with an opening formed therein, a guard electrode covering the opening, a filter insulator over the guard electrode, a cathode over the filter insulator, respective first and second electrical conductor means carried by the body and terminating at the bottom face thereof, means including a first wire disposed adjacent to the bottom face and electrically connecting the first conductor to the guard electrode, a first compression ring concentrically of the guard electrode and bearing against the first wire, means including a second wire electrically connecting the second conductor to the cathode, a second compression ring concentrically of the first ring and radially thereof, thereby retaining a portion of the second wire against the bottom face, the second wire running between the first and second compression rings and substantially along the outer face of the first compression ring, and a bottom disc secured to the body and retaining the cathode and the compression rings therebetween.

5. In an oxygen sensing cell, the combination of a body having a central cavity, the body further having an end face with an opening formed therein, the opening communicating with the cavity in the body, a button having a hollow sleeve portion press-fitted within the opening, the button further having a head portion with at least one aperture formed therein, a cathode covering the opening in the end face of the body outwardly of the head portion of the button, a spool in the central cavity of the body, the spool having an opening formed therein and press-fitted over the sleeve portion of the button, thereby retaining the spool in the cavity and coaxially of the button, and an anode comprising a helical wire wound about the spool.

6. A polarographic oxygen sensing cell, comprising a generally cylindrical body having respective top and bottom portions, the body having an enlarged bore forming a central cavity therein, the body further having a counterbore in its top portion, an annular ledge between the bore and counterbore, a compensation membrane mounted on the ledge, an O-ring on top of the compensation membrane, a p.c. board on top of the O-ring, a top disc secured within the top of the body, the disc having a portion bearing against the p.c. board, thereby resiliently retaining the p.c. board and the compensation membrane, the bottom portion of the body having an end face, the end face having an opening formed therein communicating with the cavity, a cathode across the opening in the body, the cathode including a permeation sense membrane and a mesh electrode secured thereto, a guard electrode between the opening and the cathode and insulated therefrom, whereby oxygen molecules dissolved in the electrolyte and diffusing towards the cathode will be scavenged by the guard electrode, means including a bottom disc secured to the body for retaining the cathode and the guard electrode, the bottom disc having a central opening therein communicating with the sense membrane, a hollow spool mounted within the cavity concentrically of the opening in the bottom portion of the body, an anode comprising a wire wound about the spool, an electrolyte within the cavity in the body, and respective conductor means carried by the body and electrically connecting the p.c. board to the anode, cathode, and guard electrode, respectively.

* * * * *